(12) United States Patent
Thomas et al.

(10) Patent No.: US 11,696,747 B2
(45) Date of Patent: Jul. 11, 2023

(54) DEVICES AND METHODS FOR SEMEN ANALYSIS

(71) Applicant: Nanovare SAS, Lyons (FR)

(72) Inventors: Daniel Thomas, Lyons (FR); Mohamed Hamza, Lyons (FR); Fanny Chesa, Castries (FR)

(73) Assignee: Nanovare SAS, Lyons (FR)

( * ) Notice: Subject to any disclaimer, the term of this patent is extended or adjusted under 35 U.S.C. 154(b) by 295 days.

(21) Appl. No.: 16/650,032

(22) PCT Filed: Sep. 29, 2017

(86) PCT No.: PCT/IB2017/001347
§ 371 (c)(1),
(2) Date: Mar. 24, 2020

(87) PCT Pub. No.: WO2019/064040
PCT Pub. Date: Apr. 4, 2019

(65) Prior Publication Data
US 2020/0278284 A1    Sep. 3, 2020

(51) Int. Cl.
*A61B 10/00* (2006.01)
*B01L 3/00* (2006.01)
(Continued)

(52) U.S. Cl.
CPC ...... *A61B 10/0058* (2013.01); *B01L 3/50273* (2013.01); *B01L 3/502715* (2013.01);
(Continued)

(58) Field of Classification Search
CPC ............ G01N 15/1434; G01N 33/487; G01N 2800/367; B01L 3/502715; B01L 3/50273;
(Continued)

(56) References Cited

U.S. PATENT DOCUMENTS

| 4,402,614 A | 9/1983 | Porath-Furedi |
| 4,896,966 A | 1/1990 | Boisseau et al. |

(Continued)

FOREIGN PATENT DOCUMENTS

| EP | 0256867 A2 | 2/1988 |
| EP | 0538394 B1 | 4/1993 |

(Continued)

OTHER PUBLICATIONS

Agrawal et al., 1993, "Mining association rules between sets of items in large databases". Proceedings of the 1993 ACM SIGMOD international conference on Management of data—SIGMOD '93. pp. 207-216.

(Continued)

*Primary Examiner* — Michael P LaPage
(74) *Attorney, Agent, or Firm* — Brown Rudnick LLP; Adam M. Schoen

(57) ABSTRACT

Provided herein are devices and methods for analysis of male fertility. The invention provides self-contained, handheld receptacles and systems for collection and analysis of semen samples and methods of using such devices to analyze semen samples. Also provided are processor-implemented and machine learning methods of analyzing semen sample data obtained using devices of the invention.

14 Claims, 11 Drawing Sheets

(51) Int. Cl.
 *G01N 15/14* (2006.01)
 *G01N 33/487* (2006.01)
(52) U.S. Cl.
 CPC ....... *G01N 15/1434* (2013.01); *G01N 33/487* (2013.01); *B01L 2300/023* (2013.01); *B01L 2300/0627* (2013.01); *B01L 2300/0654* (2013.01); *B01L 2300/168* (2013.01); *B01L 2400/0475* (2013.01); *G01N 2800/367* (2013.01)
(58) Field of Classification Search
 CPC ....... B01L 2300/023; B01L 2300/0627; B01L 2300/0654; B01L 2300/168; B01L 2400/0475; A61B 10/0058
 See application file for complete search history.

(56) References Cited

U.S. PATENT DOCUMENTS

| | | | |
|---|---|---|---|
| 4,896,967 | A | 1/1990 | Douglas-Hamilton et al. |
| 5,427,946 | A | 6/1995 | Kricka et al. |
| 5,744,366 | A | 4/1998 | Kricka et al. |
| 5,770,363 | A | 6/1998 | Brown |
| 5,837,197 | A | 11/1998 | Porrazzo et al. |
| 5,866,354 | A | 2/1999 | Froman |
| 6,426,213 | B1 | 7/2002 | Eisenson |
| 6,454,756 | B1 | 9/2002 | Sasaki |
| 6,593,139 | B1 | 7/2003 | Yanagimachi et al. |
| 6,596,310 | B1 | 7/2003 | Chou et al. |
| 6,929,945 | B2 | 8/2005 | Aravanis et al. |
| 7,108,966 | B2 | 9/2006 | Aravanis et al. |
| 7,195,920 | B2 | 3/2007 | Seidel et al. |
| 7,252,642 | B2* | 8/2007 | Kislev ................. G01N 21/0303 422/82.05 |
| 7,720,272 | B2 | 5/2010 | Armogida |
| 8,206,988 | B2 | 6/2012 | Durack et al. |
| 8,211,629 | B2 | 7/2012 | Schenk et al. |
| 8,390,681 | B1 | 3/2013 | Burkman et al. |
| 8,535,622 | B2 | 9/2013 | Shany et al. |
| 8,550,119 | B2 | 10/2013 | Unger et al. |
| 8,617,904 | B2 | 12/2013 | Durack et al. |
| 8,637,471 | B2 | 1/2014 | Karehed et al. |
| 8,639,043 | B2 | 1/2014 | Levenson et al. |
| 8,765,365 | B2 | 7/2014 | Schenk et al. |
| 8,975,035 | B2 | 3/2015 | Sharpe et al. |
| 9,023,613 | B2 | 5/2015 | Tseng et al. |
| 9,034,161 | B2 | 5/2015 | Carrell et al. |
| 9,074,183 | B2 | 7/2015 | Abed |
| 9,340,762 | B2 | 5/2016 | Sun et al. |
| 9,445,840 | B2 | 9/2016 | Han et al. |
| 9,453,242 | B2 | 9/2016 | Nakagata et al. |
| 9,499,778 | B2 | 11/2016 | Palermo |
| 9,663,755 | B2 | 5/2017 | Nosrati et al. |
| 9,757,726 | B2 | 9/2017 | Sharpe et al. |
| 9,784,961 | B2 | 10/2017 | Wooder et al. |
| 10,371,622 | B2 | 8/2019 | Sharpe et al. |
| 10,400,213 | B2 | 9/2019 | Evans et al. |
| 10,417,481 | B2* | 9/2019 | Shafiee ................. H04N 5/2256 |
| 10,422,737 | B2 | 9/2019 | Demirci et al. |
| 10,465,164 | B2 | 11/2019 | Dendukuri et al. |
| 10,470,798 | B1 | 11/2019 | Navarrete Solano et al. |
| 2011/0061472 | A1* | 3/2011 | Wo ........................ G01N 35/00 73/863.21 |
| 2012/0052485 | A1 | 3/2012 | Shany et al. |
| 2012/0118740 | A1* | 5/2012 | Garcia .................. G01N 15/00 204/547 |
| 2013/0194410 | A1* | 8/2013 | Topman .................... G06T 7/44 382/133 |
| 2013/0253457 | A1* | 9/2013 | Shubin, Sr. ............. A61F 5/453 604/349 |
| 2014/0248656 | A1 | 9/2014 | Demirci et al. |
| 2014/0273179 | A1* | 9/2014 | Sharpe ................... C12N 5/061 435/283.1 |
| 2015/0233927 | A1* | 8/2015 | Giannakakou ..... G01N 21/6458 435/7.1 |
| 2016/0174902 | A1 | 6/2016 | Georgescu et al. |
| 2016/0290913 | A1* | 10/2016 | Demirci ................. G01N 15/00 |
| 2017/0053398 | A1 | 2/2017 | Mahoor et al. |
| 2017/0146508 | A1 | 5/2017 | Deshpande et al. |

FOREIGN PATENT DOCUMENTS

| | | |
|---|---|---|
| EP | 1395810 A1 | 3/2004 |
| EP | 2404579 A1 | 1/2012 |
| EP | 1054948 B1 | 4/2014 |
| EP | 2716300 A1 | 4/2014 |
| WO | 2016182551 A1 | 11/2016 |
| WO | 2017055581 A1 | 4/2017 |

OTHER PUBLICATIONS

Ben-Hur et al., 2001, Support Vector Clustering, Journal of Machine Learning Research, 2:125-137.
Bhalodiya et al., 2013, An Efficient way to Find Frequent Pattern with Dynamic Programming Approach [1], Nirma University International Conference on ENgineering, NUiCONE-2013, pp. 28-30.
Breiman, 2001. Random Forests, Machine Learning 45:5-32.
Charniak, 1991, E. Bayesian Networks without Tears, AI Magazine, Winter 1991, pp. 50-63.
Deng et al, 2014, Fast mining frequent itemsets using Nodesets.[2]. Expert Systems with Applications, 41(10): 4505-4512.
Deng et al., 2012, A New Algorithm for Fast Mining Frequent Itemsets Using N-Lists [3]. Science China Information Sciences, 55 (9): 2008-2030.
Han, 2000, Mining Frequent Patterns Without Candidate Generation, Proceedings of the 2000 ACM SIGMOD International Conference on Management of Data. SIGMOD '00: 1-12.
International Search Report and Written Opinion issued in International Application No. PCT/IB2017/001347, dated Jul. 6, 2018, 9 pages.
Krizhevsky et al., 2012, Imagenet classification with deep convolutional neural networks, in Pereira, et al. Eds., Advances in Neural Information Processing Systems 25, Curran Associates, Inc., pp. 1097-3105.
Muggleton et al., 1994, Inductive Logic Programming: Theory and methods, The Journal of Logic Programming. 19-20: 629-679.
Press et al., 2007, Section 16.5. Support Vector Machines. Numerical Recipes: The Art of Scientific Computing (3rd ed.) New York: Cambridge University, 1262 pages.
Segerink et al., 2010, On-chip determination of spermatozoa concentration using electrical impedance measurements, Lab on a Chip, vol. 10, No. 8, Feb. 4, 2010, p. 1018-1024.
Shi et al., 2006, Unsupervised Learning with Random Forest Predictors, Journal of Computational and Graphical Statistics, 15(1):118-138.
Simonyan et al.,2014, Very deep convolutional networks for large-scale image recognition, CoRR, abs/3409.1556, 14 pages.
Szegedy et al., 2015, Going deeper with convolutions, in CVPR 2015, 9 pages.
Wang et al., 2015, Face Search at Scale: 80 Million Gallery, 14 pages.

* cited by examiner

DEVICES AND METHODS FOR SEMEN ANALYSIS

FIELD OF THE INVENTION

The invention relates generally to devices and methods for analysis of male fertility.

BACKGROUND

The desire to have children is both innate and cultural, and many adults describe raising children as among the most fulfilling experiences in their lives. However, many couples are unable to conceive a child, and the emotional toll of infertility can be devastating. Over the last several decades, the average age of first-time mothers has steadily increased, as couples postpone having children for financial and social reasons. Concomitantly, women's reproductive health has become a focus of medical attention due to the decrease in fecundity as women age, but less emphasis has been placed on male fertility. Nevertheless, half of infertility problems are attributable to men's medical issues, and each year more than 140 million men are unable to conceive a child.

Existing methods for diagnosing male infertility are plagued by a plethora of problems. First, providing semen samples can be isolating and humiliating. Typically, a man has to provide a semen sample in a clinical environment where he is isolated from his partner. In addition, most analyses of semen samples take hours or days and must be carried out by a trained professional, so the patient may have to wait weeks before he can learn the results. Moreover, the results may be inconclusive because a variety of abnormalities, such as low sperm number, poor sperm motility, and aberrant sperm morphology, can cause infertility. Yet, many semen analysis tests look at only one or two of these factors. Thus, the patient may have to undergo repeated cycles of providing samples and waiting for results while different types of tests are performed. Finally, the requirement for sophisticated equipment and trained personnel makes testing for male infertility expensive, whether the cost is borne by the individual or an insurance network, and many people lack the resources to obtain fertility testing. Consequently, many men forego fertility testing altogether and, along with their partners, resign themselves to lives without children.

SUMMARY

The invention provides a fully integrated semen analysis system that can be used by a male in the privacy of his own home. The device includes a receptacle that is configured to receive a sperm sample and that is also configured to be directly coupled to an analytical component that analyzes important characteristics of sperm associated with infertility, e.g., sperm number, sperm motility, and sperm morphology. The device is a turn-key instrument that requires no training for use. A sample is provided and analyzed with a touch of a button with results provided instantly to an electronic device owned by the man, such as a smart-phone or laptop computer. In that manner, a man can avoid a clinical setting to provide a semen sample and can have his sample instantaneously analyzed by the device to obtain clinical laboratory quality results without having to leave his home.

Aspects of the invention are accomplished with the self-contained, hand-held systems and devices of the invention for collecting and analyzing semen samples. The systems include a receptacle that has an opening that can accommodate at least a tip of a penis, a fluidic chamber for collection of the semen sample, and a microfluidic element in which a portion of the sample can be analyzed. Attached to the receptacle, preferably in removable manner, is an analytical device that includes an optical device and a processor. The optical device, which may include a complementary metal oxide semiconductor (CMOS) sensor, is positioned to record information from the portion of the sample in the microfluidic element of the receptacle. The processor receives optical data from the optical device to determine sperm number, sperm morphology, and sperm motility of the semen sample. The analytical device may include a transmitter that can transmit data on the semen sample to a remote device. The invention also provides methods of using such systems and devices to analyze semen samples.

The systems, devices, and methods of the present invention afford quick, convenient, and private collection and analysis of semen samples. The apparatuses can be held in the hand of the user and do not need to interface with specialized medical machinery, so they can be used in a location convenient for the user, such as in the home. In addition, the systems and devices provide rapid determination of sperm number, sperm morphology, and sperm motility of the semen sample in a fully automated manner. Thus, the user can obtain a comprehensive analysis of his fertility profile, in some cases within minutes. Moreover, because the systems and devices are self-contained, they do not require external transfer of the semen sample. As a result, manipulations that can affect the integrity of the sample are avoided, leading to increased accuracy and ease of use. In addition, by obviating the need for external transfer of a semen sample, the devices minimize the risk of exposure to sexually-transmitted pathogens when the devices are handled by a second party. In systems in which the receptacle is removable from the analytical device, the analytical component can be reused simply by replacing the receptacle, which may be helpful if the man is required to provide an additional semen sample.

In certain embodiments, the invention provides a system for collection and analysis of a semen sample. The system includes a receptacle and an analytical device that includes an optical device and a processor. The optical device is positioned to record information from a portion of a semen sample in the receptacle. The processor is configured to receive optical data from the optical device and determine sperm number, sperm morphology, and sperm motility of the semen sample. Preferably, the receptacle is removable from the analytical device.

The receptacle includes a macrofluidic fluidic chamber, e.g., larger than the microfluidic scale, for collection of the semen sample. The receptacle may be of any suitable shape and dimensions to accommodate a portion of penis, e.g., the tip of a penis, and to be held in the hand of a user. For example, the receptacle may generally have the shape of a cylinder, cone, cube, box, ovoid, etc., and the receptacle may be able to hold at least about 1 ml, about 2 ml, about 5 ml, about 10 ml, about 20 ml, about 50 ml, about 100 ml, or more (e.g., macrofluidic). The interior walls of the receptacle may have a reflective coating that reflects light from the analytical device toward a portion of the semen sample, e.g., the portion from which the optical device records information. The interior walls of the receptacle may have a coating that prevents semen from adhering to them. Such a coating facilitates movement of the semen sample into the microfluidic element in the receptacle. The coating may or may not be combined with an active or passive pump to facilitate movement of the semen sample into the microfluidic element, which will be discussed in more detail below.

The receptacle includes an opening through which the semen sample is collected. Thus, the opening is shaped and dimensioned to accommodate a portion of a penis, e.g., the tip of a penis. Preferably, the opening is dimensioned to accommodate a portion of a penis, e.g., the tip of a penis, with an air gap between the portion of the penis and the opening. For example, the opening may be circular, oval, square, rectangular, etc. and may have a longest diameter of at least about 5 cm, about 10 cm, about 15 cm, about 20 cm, about 25 cm, or more. The opening may be at any suitable position in the receptacle in relation to the attached analytical device. For example, if the system is positioned with the analytical device attached to the bottom of the receptacle, the opening may on a side or the top of the receptacle. Preferably, the opening is lined with an elastomeric material that can contact a penis without scratching, cutting, or chafing it or otherwise cause discomfort to the user. For example, the opening may be lined with silicone, plastic, rubber, or the like.

The receptacle includes a microfluidic element (e.g., on the microliter scale) in which a portion of the semen sample may be analyzed. The microfluidic element is in fluidic connection with the macrofluidic fluidic chamber. The microfluidic element and macrofluidic fluidic chamber may be separated by a valve or the like which allows opening and closing of the fluidic connection between the microfluidic element and macrofluidic fluidic chamber. The microfluidic element is positioned with the receptacle so that the optical device in the analytical device may record information from it. For example, if the system is positioned with the analytical device attached to the bottom of the receptacle, the microfluidic element may be located at the bottom portion of the receptacle in proximity to the optical device, or the microfluidic element may be located on a side or top portion of the receptacle.

The receptacle may include a lid that covers the opening. When secured, the lid prevents fluid exchange between the macrofluidic fluidic chamber and the exterior of the receptacle and thus prevents the semen sample from flowing out of the receptacle. Preferably, the lid is removable. The lid may have any shape and dimensions suitable for covering the opening. Preferably, the lid has a shape and dimensions complementary to those of the opening. The lid may also provide an air-tight seal and may also act as a pump, such that attachment of the lip creates a seal and pressure difference within the receptacle, driving a portion of the semen sample into the microfluidic element.

The optical device may include a lens system. The lens system may be in a portion of the optical device proximal to the receptacle. The lens system may include a magnifying lens, such as a microscope lens. The lens system may include a central magnifying lens surrounded by an opaque material. The lens system may include a translucent material adjacent to the receptacle-proximal side of the magnifying lens.

The optical system includes a sensor on the receptacle-distal side of the lens system. The sensor senses light signals that pass from the semen sample through the lens system. The sensor may be a complementary metal oxide semiconductor (CMOS), charge-coupled device, colorimeter, contact image sensor, electro-optical sensor, infrared sensor, fiber optic sensor, optical position sensor, photodetector, photodiode, photomultiplier tubes, phototransistor, photoelectric sensor, photoionization detector, photomultiplier, photoresistor, photoswitch, or phototube.

The analytical device may include a lighting system. The lighting system includes a light source. The lighting system may include optical fibers that transmit light from the light source to the receptacle or a portion of the receptacle.

The analytical device may include a transmitter capable of transmitting data from the processor to a remote device. The transmitter may transmit information about one or more of sperm number, sperm morphology, and sperm motility of the semen sample The system may include a pump (active or passive) coupled to the receptacle and capable of transporting a portion of the semen sample from the macrofluidic fluidic chamber into the microfluidic element.

In another aspect, the invention provides receptacles for collection and analysis of a semen sample. The receptacle may include any element described above in relation to the receptacle component of the system for collection and analysis of a semen sample.

In another aspect, the invention provides methods of analyzing a semen sample from a subject using a device of the invention. The methods may include at least the following steps: providing a device configured to be held in the hand of a user, the device including a receptacle, an optical element, and a processor; receiving a semen sample in the receptacle; and determining information about the sperm number, sperm morphology, and sperm motility of the sample using the optical element and the processor in the device. In certain embodiments, the methods are performed without any external (i.e., outside of the device) preparation of the semen sample. Preferably, the methods are performed without transferring the semen sample outside of the device. The receptacle may be removable from the optical element and processor, and the methods may be performed while the receptacle is separated from the optical element and processor of the device. Additionally or alternatively, the methods may be performed while the receptacle is attached to the optical element and processor of the device.

The device of the methods may include any elements described above in relation to the systems and devices of the invention. Preferably, the device of the methods is configured to receive a portion of a penis, e.g., a tip of a penis. The receptacle may be removable from the optical element and the processor. The optical element and the processor may be housed in an analytical device.

The semen sample may be received in the receptacle while the receptacle is attached to the optical element and the processor. Alternatively, the semen sample may be received in the receptacle while the receptacle is separated from the optical element and the processor, and the receptacle may be subsequently attached to the optical element and the processor.

The methods may include transmitting information about the sperm number, sperm morphology, and sperm motility of the sample to a remote device.

The methods may include transferring a portion of the semen sample from a macrofluidic fluidic chamber to a microfluidic element within the device. Transferring of the semen sample may be achieved by an active or passive means. Active transfer may include pumping, applying pressure, or mechanical action. Passive transfer may include a step that facilitates flow of the sample, such as adding a viscosity-altering agent to the semen sample within the device. The viscosity-altering agent may be a liquefying agent, surfactant, soap, or detergent.

The methods may be performed without heating the semen sample.

In another aspect, the invention provides methods of analyzing a semen sample from a subject using one or more processors. The methods may include the following steps:

capturing sequential images of the sample at defined intervals; identifying individual sperm cells in the images; correlating the identity of individual sperm cells between different images; counting individual sperm cells in at least one or more images to obtain one or more image sperm numbers; measuring the shape and size of individual sperm cells in at least one image to obtain individual sperm cell morphologies; measuring positions of individual sperm cells in two or more images in which an individual sperm cell appears; determining from the positions of the sperm cells and the defined interval individual sperm cell motilities; and using the image sperm numbers, the individual sperm cell morphologies, and the individual sperm cells motilities to determine the sperm number of the semen sample, the sperm morphology of the semen sample, and the sperm motility of the semen sample.

The intervals between sequentially captured images of the semen sample may be any suitable interval for determining sperm motility. For example, the image capture rate may be about $10 \text{ s}^{-1}$, $20 \text{ s}^{-1}$, $30 \text{ s}^{-1}$, $60 \text{ s}^{-1}$, $90 \text{ s}^{-1}$, $150 \text{ s}^{-1}$, $300 \text{ s}^{-1}$, $600 \text{ s}^{-1}$, or $900 \text{ s}^{-1}$.

Sperm motility may reflect speed, direction of movement, or both. Thus, sperm motility may be expressed as a vector.

Within a set of images of a given sample, sperm number, sperm morphology, or both may be determined for a subset of the images. For example, sperm number or morphology may be determined for only 1 of every 2, 3, 4, 5, 6, 8, 10, or more images.

In another aspect, the invention provides methods of evaluating male fertility using a machine learning system using data from semen samples. The methods may include the following steps: providing to the machine learning system data from semen samples from training subjects and fertility status of the training subjects to allow the machine learning system to detect features within the semen sample data and autonomously learn associations between the features and fertility status; providing to the machine learning system data from a semen sample from a test subject; and using the machine learning system to determine the fertility status of the test subject based on detection of one or more observed features in the semen sample data from the test subject.

In another aspect, the invention provides methods of evaluating male fertility using a machine learning system using data from semen samples in combination with one or more other types of data, such as genetic data, health data, medical data, and lifestyle data. The methods may include the following steps: providing to a machine learning system data from semen samples from training subjects, one or more other data sets from the training subjects, and fertility status of the training subjects to allow the machine learning system to detect features within the semen sample data and the one or more other data sets and autonomously learn associations between the features and the fertility status; providing to the machine learning system data from a semen sample from a test subject and one or more other data sets from the test subject; and using the machine learning system to determine the fertility status of the test subject based on detection of one or more observed features in the data from the test subject.

In another aspect, the invention provides methods of suggesting a course of treatment for male infertility using data from semen samples. The methods may include the following steps: providing to a machine learning system data from semen samples from training subjects, treatment methods used to treat the training subjects, and procreative outcomes of the training subjects to allow the machine learning system to detect features within the semen sample data and autonomously learn associations between the features, treatment methods, and procreative outcome; providing to the machine learning system data from a semen sample from a test subject; and using the machine learning system to suggest a treatment method for the test subject based on detection of one or more observed features in the semen sample data from the test subject.

In another aspect, the invention provides methods of suggesting a course of treatment for male infertility using data from semen samples in combination with one or more other types of data, such as genetic data, health data, medical data, and lifestyle data. The methods may include the following steps: providing to a machine learning system data from semen samples from training subjects, one or more other data sets from the training subjects, treatment methods used to treat the trainings subjects, and procreative outcomes of the training subjects to allow the machine learning system to detect features within the semen sample data and other data sets and autonomously learn associations between the features, treatment methods, and procreative outcome; providing to the machine learning system data from a semen sample and one or more other data sets from a test subject; and using the machine learning system to suggest a treatment method for the test subject based on detection of one or more observed features in the data from the test subject.

DETAILED DESCRIPTION

The invention provides devices and methods that allow quick, convenient, and private collection and analysis of semen samples. The devices are portable, self-contained, and do not require specialized medical equipment or highly trained personnel. Consequently, the user can provide a sample and obtain the results at the time and place of his choice. Because the devices and methods evaluate sperm number, sperm morphology, and sperm motility in a semen sample, they provide a comprehensive analysis of key factors that affect male fertility and give the user actionable insights on how to overcome barriers to conceiving a child.

Figure 1:
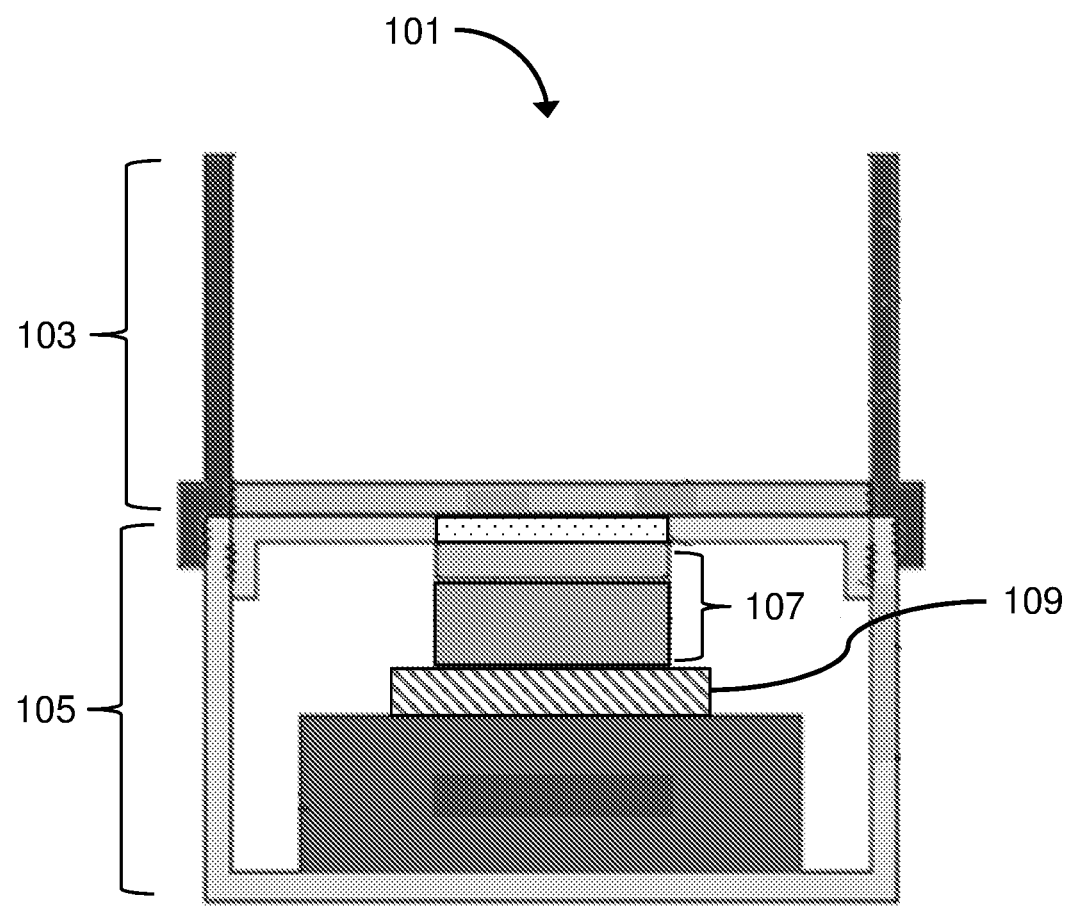
FIG. 1 shows a system for analyzing a semen sample according to an embodiment of the invention.

FIG. 1 shows a system 101 for analyzing a semen sample according to an embodiment of the invention. The system includes a receptacle 103 configured to receive a semen sample. The system also includes an analytical device 105 attached to the receptacle 103. The analytical device 105 includes an optical device 107 positioned to interrogate a portion of the semen sample and a sensor 109 configured to receive optical data from the optical device 107. Preferably, the receptacle 103 is detachable from the analytical device 105.

Figure 2:
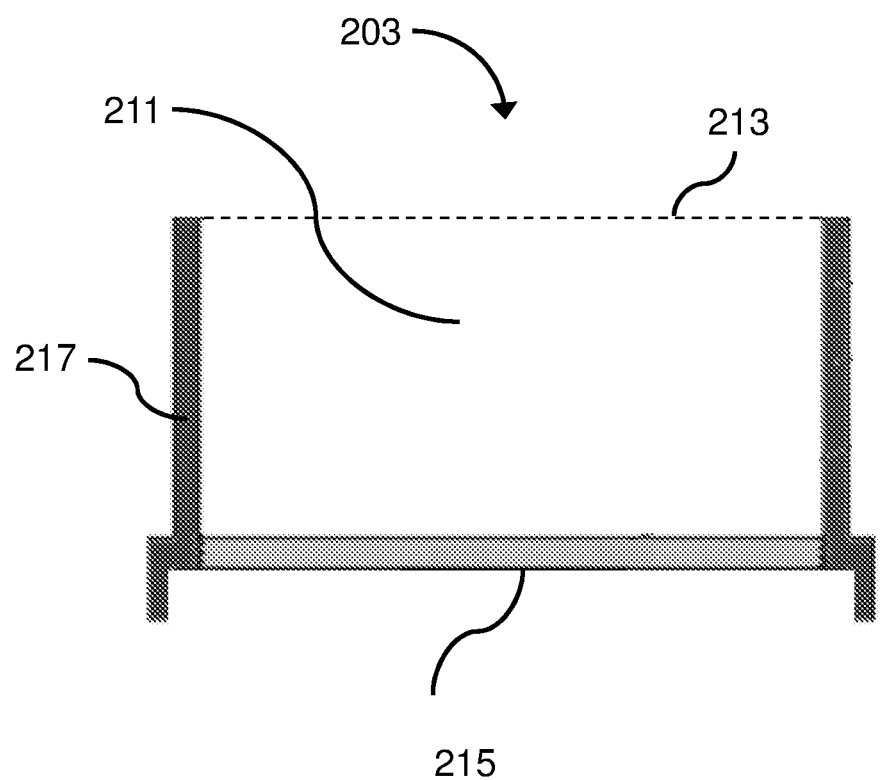
FIG. 2 shows a receptacle for a semen sample according to an embodiment of the invention.

FIG. 2 shows a receptacle 203 for a semen sample according to an embodiment of the invention. The receptacle 203 includes a macrofluidic fluidic chamber 211 that receives the semen sample. As used herein, "macrofluidic" refers to a volume of at least one or more milliliters, up to and including liters of fluid. For example, a macrofluidic chamber of channel is a chamber or channel dimensioned to hold one or more milliliters, up to and including liters, of fluid Thus, a macrofluidic receptacle may have a volume of at least about 1 ml, at least about 2 ml, at least about 5 ml, at least about 10 ml, at least about 20 ml, at least about 50 ml, at least about 100 ml, at least about 1,000 ml or more.

As used herein, "microfluidic" refers to a volume on the microliter scale. For example, a microfluidic chamber of channel is a chamber or channel dimensioned to hold one or more microliters of fluid, up to a milliliter of fluid. A microfluidic chamber of channel can hold a volume of less than microliters, such as nanoliters of fluid.

The receptacle 203 includes a chamber opening 213 that creates a fluidic connection between the chamber 211 and the exterior of the receptacle 203. The opening 213 is shaped and dimensioned to accommodate a portion of a penis, e.g., the tip of a penis, so that the user may ejaculate directly into the chamber 211. This obviates the need to collect the semen sample outside the receptacle and subsequently transfer the sample into the receptacle. In addition, to provide both physical and psychological comfort to the user, it is desirable for the receptacle to make minimal contact with the user's penis while the user is providing a sample. Thus, in preferred embodiments, the receptacle can accommodate the tip of a penis with an air gap between the penis and one or more walls 217 of the receptacle, either at the opening 213 and within the chamber 211. For example, the opening may be circular, oval, square, rectangular, etc. and may have a longest diameter of at least about 5 cm, about 10 cm, about 15 cm, about 20 cm, about 25 cm, or more. Also for the user's comfort, the opening may be lined with an elastomeric material, such as silicone, plastic, rubber, or the like, that can contact a penis without scratching, cutting, or chafing it. For example, the opening may be circular and have a silicone, plastic, or rubber ring at its edge. As illustrated, the opening 213 is at the top of the receptacle, but the opening 213 may be situated in the side or any other suitable portion of the receptacle.

The receptacle 203 also includes a microfluidic element 215 in fluidic connection with the chamber 211. The microfluidic element 215 is configured to receive a portion of the semen sample. The fluidic connection between the microfluidic element 215 and the chamber 211 may persist, or the microfluidic element 215 and the chamber 211 may be separated by a valve or similar device that allows the fluidic connection to be opened and closed. The microfluidic element includes a detection zone in which a portion of the semen sample can be analyzed by the analytical device. The wall of the microfluidic element situated between the detection zone and the analytical device is transparent so that light can pass from the portion of the sample in the detection zone into the optical device. The detection zone is dimensioned to accommodate a known volume so that the number of sperm cells counted in a portion of the detection zone can be extrapolated to determine the sperm number of the semen sample. As used herein, the sperm number of a semen sample refers to the number of sperm cells per unit of volume of semen and is used interchangeably with sperm count and sperm/semen density. The detection zone may include one or more reference objects of known dimensions and/or position to allow scaling and registration of images captured by the optical device.

The microfluidic element 215 may be made of hard material, such as silicon, or elastomeric material, such as silicone rubber. Manufacture of microfluidic elements from elastomeric materials by soft lithography is described in U.S. Pat. No. 8,550,119, which is incorporated herein by reference. The microfluidic element 215 may contain a semi conductive material, such as polysilicon, silicon nitride, silicon dioxide, or a metal, and may be magnetic or electrically conductive. The microfluidic element 215 may contain a valve that regulates, i.e., opens and closes, the fluidic connection between the microfluidic element 215 and the macrofluidic fluidic chamber 211, and it may contain one or more internal valves that regulate flow within the microfluidic element 215. One or more of the valves may be check valves that permit flow of fluids, such as semen, in only one direction through a conduit, such as those described in U.S. Pat. No. 8,550,119. In a microfluidic element 215 that contains multiple valves, the valves may be individually addressable.

Flow of fluids, e.g., semen, through the microfluidic element 215 may be actuated by active means, passive means, or a combination of the two. For example and without limitation, active means include application of fluid pressure, e.g., air pressure, electrostatic forces, and magnetic forces. For example, flow through an elastomeric microfluidic element 215 may actuated by application of fluid pressure, e.g., air pressure, to a membrane of the element, as described in U.S. Pat. No. 8,550,119. Fluid pressure may be applied from a pump/tank system, a gas tank, compressor, piston system, liquid column, one or more miniature valves, peristaltic pumps, pinch valves, or other systems known in the art. Passive actuation includes means that facilitate flow of the sample, such as adding a viscosity-altering agent to the semen sample within the device. The viscosity-altering agent may be a liquefying agent, surfactant, soap, detergent.

The receptacle 203 may include one or more walls 217 that form a boundary between the chamber 211 and the exterior of the receptacle. To facilitate collection of the semen sample at the site of fluidic connection between the microfluidic element 215 and the chamber 211, the interior surface of the wall 217 may be coated with a material that prevents the semen from adhering to the wall 217. For example, the wall 217 may be coated with nitrocellulose, polyvinyl, or another hydrophobic material. In some configurations of systems of the invention, light is transmitted from a light source in the analytical device into the receptacle, and the receptacle focuses the light on the detection zone of the microfluidic element. Thus, the interior surface of the wall 217 may be coated with a reflective material or paint.

The receptacle 203 may include a removable lid that covers the opening. The lid prevents fluid exchange between the macrofluidic fluidic chamber 211 and the exterior of the receptacle 203. The lid may attach to the receptacle by any suitable means, such as a threaded screwcap, a snap-type cap, or the like.

Figure 3:
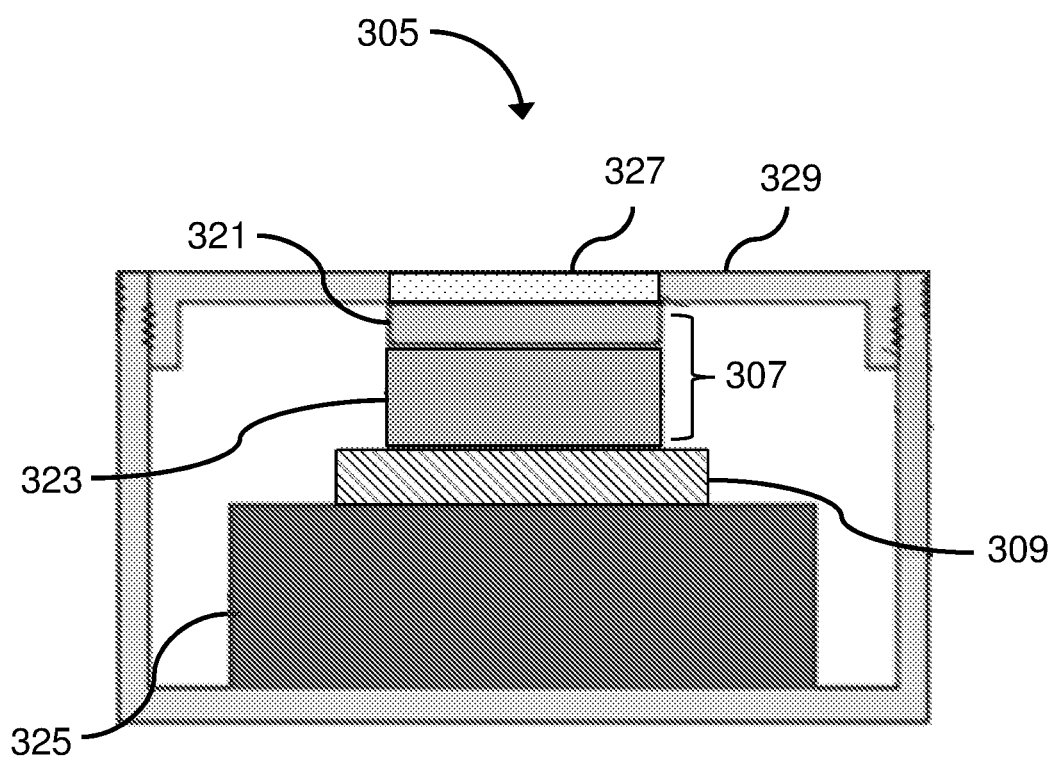
FIG. 3 shows a device for analyzing a semen sample according to an embodiment of the invention.

FIG. 3 shows a device 305 for analyzing a semen sample according to an embodiment of the invention. The analytical device 305 includes an optical device 307. The optical device includes a lens system 321 and a sensor 323. The lens system 321 includes a magnifying lens that provides suitable magnification for capturing images of sperm cells and is positioned in a portion of the analytical device 305 proximal to the receptacle 203 and aligned with the detection zone of the microfluidic element 215. The sensor 323 is situated on the receptacle-distal side of the optical device 307 and is capable of detecting light signals that pass from the receptacle and through the lens system 321. For example, the sensor 323 may contain a complementary metal oxide semiconductor (CMOS), charge-coupled device, colorimeter, contact image sensor, electro-optical sensor, infrared sensor, fiber optic sensor, optical position sensor, photodetector, photodiode, photomultiplier tubes, phototransistor, photoelectric sensor, photoionization detector, photomultiplier, photoresistor, photoswitch, or phototube. The optical device 307 is configured to capture images of the semen sample in the detection zone at periodic intervals. The interval is the inverse of the image capture rate, and either parameter may be used to express the frequency of sequentially captured images. For example, the image capture rate may be about 10 $s^{-1}$, 20 $s^{-1}$, 30 $s^{-1}$, 60 $s^{-1}$, 90 $s^{-1}$, 150 $s^{-1}$, 300 $s^{-1}$, 600 $s^{-1}$, or 900 $s^{-1}$.

The analytical device 305 includes a processor 309 configured to receive optical data from the optical device. The processor 309 has sufficient power to perform high-level, single-thread object detection and tracking. The processor 309 may be single-core or multi-core. The processor may have a speed of less than about 5 GHz, less than about 4 GHz, less than about 3 GHz, less than about 3 GHz, less than about 2 GHz, less than about 1 GHz, less than about 500 MHz, or less than about 250 MHz. Examples of processors 309 include those sold by Next Thing Co. (Oakland, Calif.) under the trade names C.H.I.P. PRO, GR8, and GR8 SOC and the processor sold under the trade name ARM CORTEX-A8 by Ann Holding (Cambridge, UK).

The analytical device 305 may include a power source 325. The power source 325 may be a battery.

The analytical device 305 may include a cover proximal to the receptacle 203. The cover may include a central, transparent portion 327 and a peripheral, opaque portion 329.

The analytical device 305 may include a lighting system. The lighting system includes a light source suitable for microscopy, such as a tungsten lamp, halogen lamp, mercury lamp, xenon lamp, or LED lamp. The lighting system may include optical fibers that transmit light from the light source to the receptacle. The optical fibers may focus the light on the microfilament element 215 or on the detection zone of the microfilament 215. The lighting system may illuminate the receptacle 203, and reflective coating on the walls 217 may focus the light on the detection zone of the microfluidic element.

The analytical device 305 may include a transmitter capable of transmitting information about sperm number, sperm morphology, or sperm motility of the semen sample to a remote device. For example, the analytical device 305 may contain a radio frequency transmitter that can send information wirelessly to a computer, mobile phone, or other hand-held device.

The system 101 may include a means for transferring a portion of the semen sample from the macrofluidic fluidic chamber 211 and the microfluidic element 215. For example, the system may include a pump coupled to the receptacle 203 to pump a portion of the semen sample into the microfluidic element 215.

Figure 4:
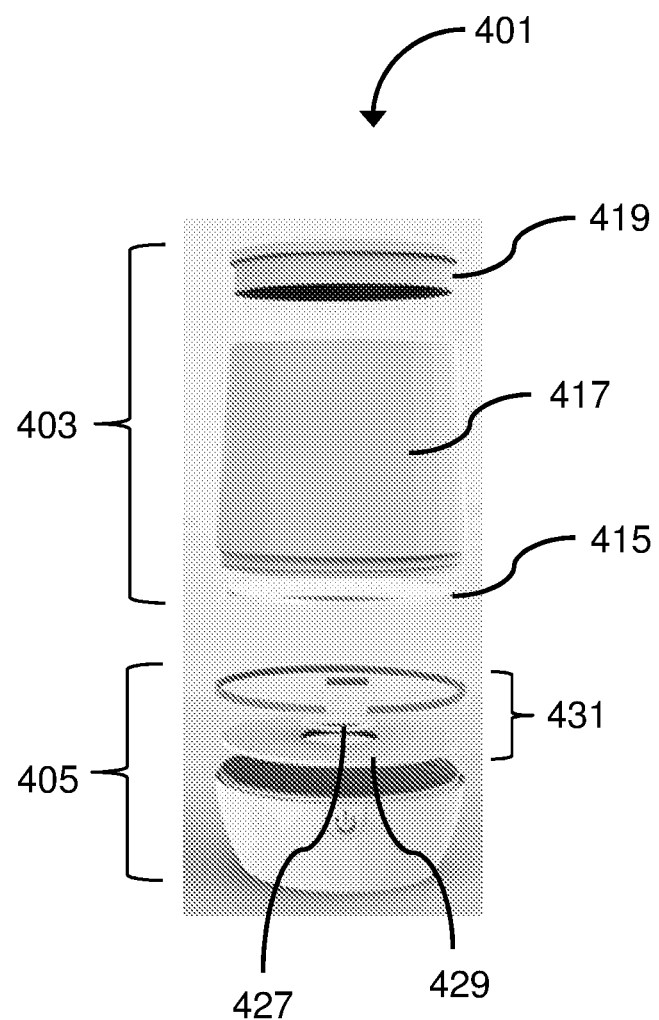
FIG. 4 is an exploded view of a system for analysis of a semen sample according to an embodiment of the invention.

FIG. 4 is an exploded view of a system 401 for analysis of a semen sample according to an embodiment of the invention. The system 401 includes a receptacle 403 and an analytical device 405. The receptacle 403 includes a wall 417 that defines a macrofluidic fluidic chamber, a microfluidic element 415, and a removable lid 419 that covers the chamber opening (not shown). The analytical device 405 may include a cover 431 that has a central, transparent portion 427 and a peripheral, opaque portion 429.

The system 401 and receptacle 403 may have any shape and dimensions that allow the devices to be held in the hand of a user while providing a semen sample. For example, the system 401 or the receptacle 403 may have a total length of less than about 10 cm, about 15 cm, about 20 cm, about 25 cm, about 30 cm, about 35 cm, about 40 cm, or about 50 cm, and a maximum diameter of less than about 5 cm, about 10 cm, about 15 cm, about 20 cm, about 25 cm, or about 30 cm. Preferably, the entire system 401 can be held in the hand of the user. Alternatively, system 401 may include a hand-held receptacle 403 that attaches to an analytical device 405, and the analytical device 405 or the entire system 401 may be too large to be held in one hand by the user.

The systems and devices of the invention may be used autonomously by the sample provider at the location of his choice, such as the home. Alternatively or additionally, the systems and devices may be used in clinical or research environments, such as hospitals, clinics, laboratories, and the like, and they may be used in to provide information to specialized personnel, such as physicians, nurses, scientists, and the like.

An advantage of the methods of the systems and devices of the inventions is that they allow quick analysis of a semen sample without external equipment. Thus, the invention also provides methods of analyzing semen samples using devices of the invention. The methods include receiving a semen sample in the receptacle of a system described above and determining the sperm number, sperm morphology, and sperm motility of the semen sample using the optical element and the processor in the analytical device.

The methods of semen analysis using the systems and devices of the invention bypass cumbersome or time-consuming steps required by previous methods. For example, the methods are performed without any external preparation of the semen sample. Preferably, the methods are performed without transferring the semen sample outside of the device. The methods may be performed without heating the semen sample.

The semen sample may be received in the receptacle while the receptacle is attached to the optical element and the processor. Alternatively, the semen sample may be received in the receptacle while the receptacle is separated from the optical element and the processor, and the receptacle may be subsequently attached to the optical element and the processor. In either instance, the method involves no preparation of the sample outside the system.

The methods may include transmitting information about the sperm number, sperm morphology, and sperm motility of the semen sample to a remote device.

The methods may include transferring a portion of the semen sample from a macrofluidic fluidic chamber to a microfluidic element within the device. Transferring of the semen sample may be achieved by an active or passive means as described above in relation to the microfluidic element 215.

Sperm number, sperm morphology, and sperm motility of semen samples may be analyzed by reference to a standard, such as the reference values adopted by the World Health Organization. WHO laboratory manual for the examination and processing of human semen, Fifth Edition, 2010, incorporated herein by reference. Under WHO standards, a semen sample is considered normal if the data for the sample is at or above the 5th percentile. According to the WHO 2010 standards, threshold values for sperm number, sperm morphology, and sperm motility are 15 million/ml, 4% normal forms, and 32% progressive motility, respectively. Thus, the analysis may indicate a percentile rank for sperm number, sperm morphology, and sperm motility individually and/or a composite value for the semen sample. The analysis may also include an indication of whether the sample is considered fertile or subfertile.

Analysis of sperm motility may include analysis of total motility percentage, progressive motility percentage, motile sperm per ejaculate, progressive velocity, mean linearity, motility index, viability percentage, or classification of motility as rapid, medium, or slow. Any of these values may be analyzed by reference to a standard. For example, according to WHO 2010 standards, threshold values for the following parameters are as follows: total motility percentage, 40%; progressive motility percentage, 32%; progressive velocity, 25 µm/s; motility index, 10; and viability, 58%.

Analysis of sperm morphology may include analysis of head size (e.g., small, normal, or large), head shape (e.g., round, tapered, amorphous), midpiece shape and size; tail shape and size; duplicate forms (multiple heads, multiple tails), or cytoplasmic droplets. Any of these values may be analyzed by reference to a standard.

The analysis of a semen sample may include analysis of the sample volume. Analysis of sample volume may also include reference to a standard, such as the WHO standard, and/or a percentile rank. According to the WHO 2010 standards, the threshold value for a normal semen sample is 1.5 ml.

The semen sample analysis may include other information related to the sample. For example and without limitation, the analysis may include information on odor, color, viscosity, liquefaction, pH, agglutination, presence of neutrophils, temperature, time since last previous emission, and method of production (e.g., masturbation, coitus interruptus, etc.) The analysis of such information may include reference to a standard value.

The invention also provides methods of analyzing a semen sample using a processor to determine sperm number, sperm morphology, and sperm motility of a semen sample. Such methods include programs performed in conjunction with a computer having a processor and a memory connected to the processor, the programs including a computer readable storage medium having a computer program mechanism encoded on it, in which the computer program mechanism may be loaded onto the memory of the computer and cause it to carry out the methods of the invention.

Figure 5:
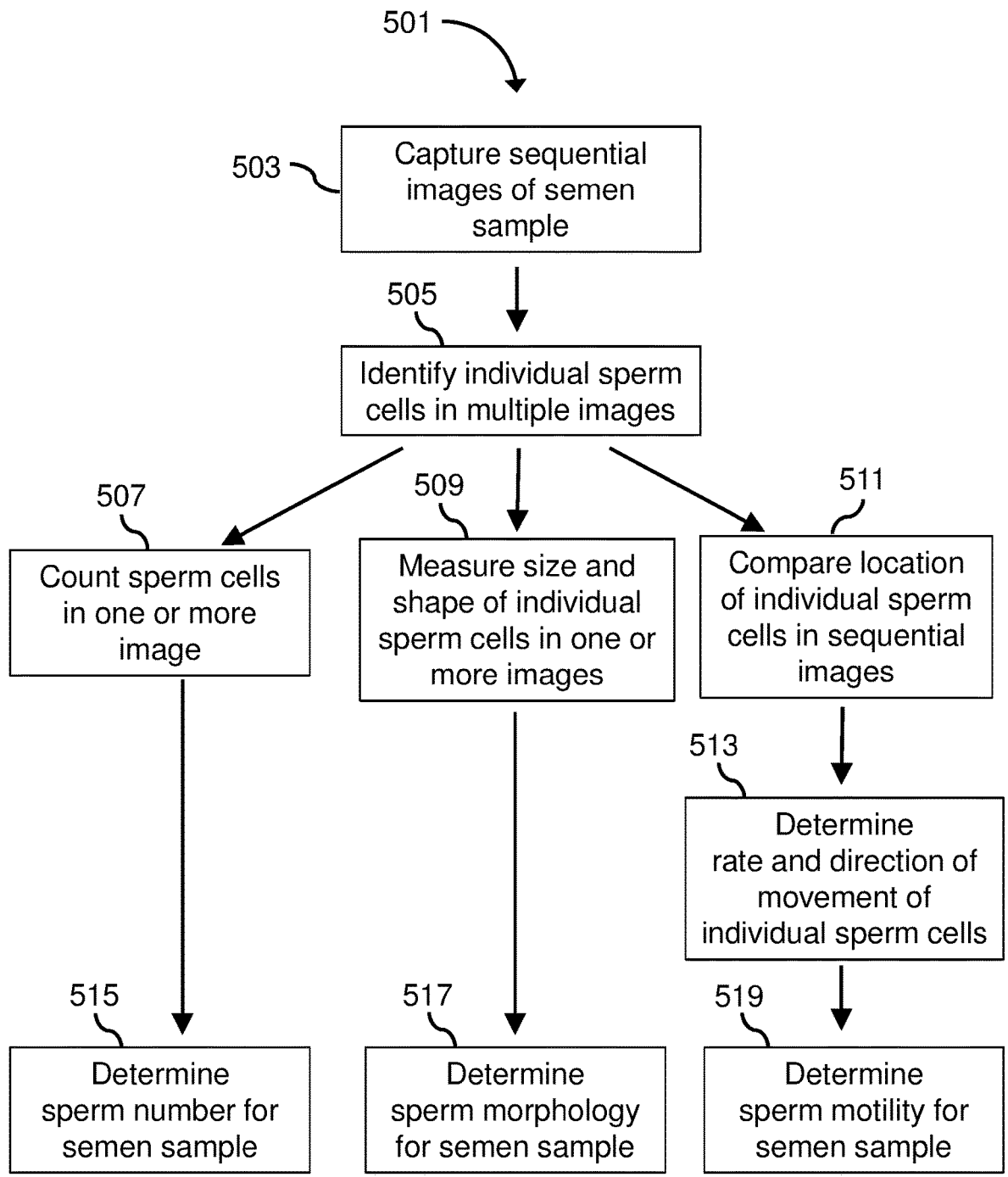
FIG. 5 is a schematic of a method of analyzing a semen sample using a processor to determine sperm number, sperm morphology, and sperm motility of a semen sample according to an embodiment of the invention.

FIG. 5 is a schematic of a method 501 of analyzing a semen sample using a processor to determine sperm number, sperm morphology, and sperm motility of a semen sample according to an embodiment of the invention. In a first step 503, sequential images of a portion of the semen sample are captured at defined intervals. The portion of the semen sample being imaged may be in the detection zone of a microfluidic element 215 of a receptacle 203, and images may be captured by an optical device 307 that includes a lens system 321 and a sensor 323. The optical data may be sent from a sensor 323 to a processor 309. The interval between sequentially captured images of the semen sample may be any suitable interval for determining sperm motility. The interval is the inverse of the image capture rate, and either parameter may be used to express the frequency of sequentially captured images. For example, the image capture rate may be about $10\ s^{-1}$, $20\ s^{-1}$, $30\ s^{-1}$, $60\ s^{-1}$, $90\ s^{-1}$, $150\ s^{-1}$, $300\ s^{-1}$, $600\ s^{-1}$, or $900\ s^{-1}$.

In another step 505, individual sperm cells are identified in multiple images. Image features such as brightness, color, pixel intensity, and the like may be used to identify sperm cells and distinguish sperm cells from debris and other objects in the sample. Individual sperm cells within an image may be tagged or coded for identification purposes. In addition, images are compared longitudinally, i.e., multiple sequential images within the sequence are analyzed, to track the location of individual sperm cells in multiple images. Register marks or other features in the images may be used to align multiple images in a sequence.

In a sequence of steps, sperm cells are counted in one or more images to determine the sperm number for the semen sample. In the first step, individual sperm cells are counted 507 in one or more images in a sequence of images. Because the images are taken from the detection zone of the microfluidic element 215 of a receptacle 203, and the detection zone has a known volume, the sperm number for the semen sample, i.e., the number of sperm cells per unit volume, can be determined 515. Statistical reliability increases as sampling increases, so it may be advantageous to analyze multiple images in counting step 507. However, increased sample also puts a greater demand on the processor and can slow the overall analysis of the semen sample, so the number of images analyzed in step 507 can be adjusted to reach the desired balance between reliability and speed of determining step 515. Thus, sperm cells may be counted 507 in only a subset of captured images. For example, sperm cells may be counted 507 only in 1 of every 2, 3, 4, 5, 6, 8, 10, or more images in a series.

In another sequence of steps, sperm cell measurements are used to determine sperm morphology for the semen sample. First, the size and shape of individual sperm cells in one or more images are measured 509. Next, individual sperm cell measurements are compiled to determine 517 sperm morphology for the semen sample. The number of individual sperm cells measured and the number of different images analyzed in step 509 influence the reliability and speed of determining step 517, so these values can be adjusted to reach the desired balance between the reliability and speed in determining step 517. Thus, sperm cells may be measured 509 in only a subset of captured images. For example, sperm cells may be measured 509 in only 1 of every 2, 3, 4, 5, 6, 8, 10, or more images in a series.

In another sequence of steps, the information regarding the position of individual sperms in sequential images is used to determine sperm motility for the semen sample. First, the location of individual sperm cells is compared 511 in sequential images. At least two sequential images should be compared, but any greater number of images can be analyzed as long as individual sperm cells can be tracked throughout the series. The positions are used to determine 513 the rate and direction of movement of individual sperm cells. Because both rate and direction of movement are determined, movement of individual sperm cells may be represented by a vector. These values are compiled to determine 519 sperm motility for the semen sample. The number of individual sperm cells tracked and the number of images in a series analyzed in steps 511 and 513 influence both the reliability and speed of determining step 519, so these values can be adjusted to reach the desired balance between reliability and speed in determining step 519.

The invention also provides machine learning systems and methods for using data from semen samples to make diagnoses or prognoses regarding the fertility status of a subject or a course of treatment to treat infertility in a subject. The data from the semen samples may be raw image data, or it may be data produced from analysis of raw image data. For example, the semen sample data may include calculated values for sperm number, sperm morphology, and sperm motility. The systems and methods may involve entering data from semen samples from subjects and outcomes, such as whether the subjects were able to conceive and by what means, from those subjects into a machine learning system. The machine learning system trains itself to represent features defined by the images and create a map of the outcome probabilities over the features. In some embodiments, the machine learning system is provided with the semen sample data and an associated outcome and allowed to autonomously identify features in the semen sample data in an unsupervised manner and then to identify predictive relationships between those identified features and the known outcome associated with the provided semen sample data. Because data from subjects with known outcomes is used to train the machine learning system, such data and subjects may be referred to as "training data" or "training subjects," respectively.

The methods may then involve entering data from semen samples from subjects for whom outcomes are unknown into the machine learning system. Because the outcomes of such individuals are unknown, such data and subjects may be referred to as "test data" and "test subjects," respectively. The machine learning system identifies predictive features in the test data, locates the features on the map of outcome probabilities, and provides a diagnoses and/or prognoses for the test subjects.

Figure 6:
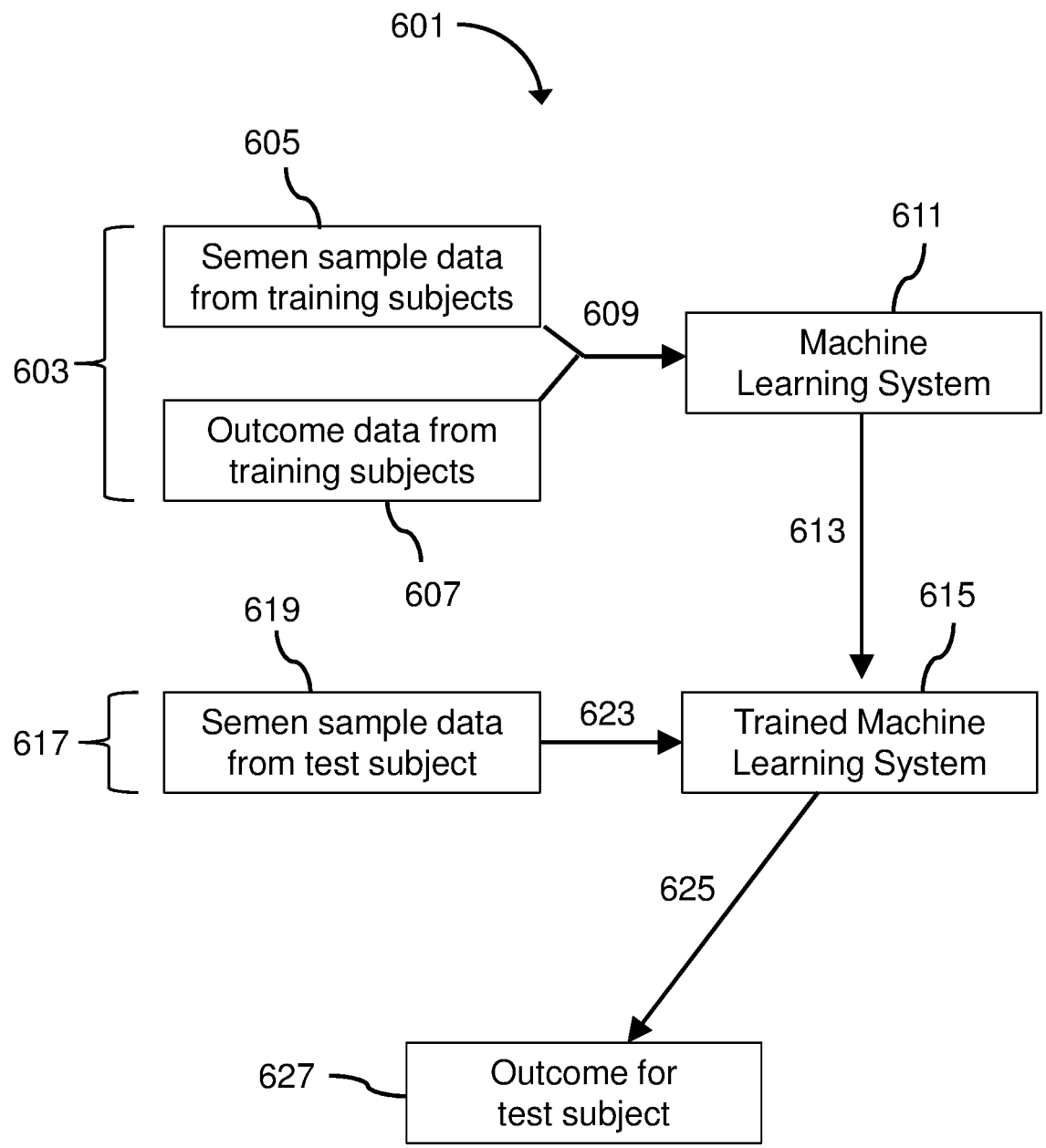
FIG. 6 illustrates a method of evaluating male fertility using a machine learning system to analyze semen sample data according to embodiments of the invention.

FIG. 6 illustrates a method 601 of evaluating male fertility using a machine learning system to analyze semen sample data according to embodiments of the invention. Training data 603, including semen sample data 605 and outcome data 607 (e.g., known fertility statuses) of the training subjects, is provided 609 to a machine learning system 611. Features are detected within the training semen sample data 605 by the machine learning system 611, which autonomously learns associations between the features and outcomes, thereby creating 613 a trained machine learning system 615. Test data 617, which includes semen sample data 619 from a test subject, is then provided 623 to the trained machine learning system 615. The trained machine learning system 615 detects features in the test semen sample data 619, correlates them with an outcome (e.g., a fertility status), and provides 625 an outcome 627 for the test subject, such as the likelihood that the test subject will be able to conceive.

The outcome data of the training subjects may be anything related to reproductive status. The outcome data may include treatment histories as well as results obtained from various types of treatment. Thus, for example and without limitation, the outcome data may include information related to one or more of the following: medications; consumption of alcohol, tobacco, and recreational drugs; diet and dietary supplements, including vitamins; physical activity levels, including exercise and fitness regimens and periods of sitting; frequency of ejaculation; frequency and timing of intercourse, including the temporal relationship between intercourse and other factors; clothing and undergarments; use of hot tubs, baths, saunas, and other environments that expose the testicles to non-physiological temperatures; surgeries, including vasectomies and vasectomy reversals, hernia repairs, correction of undescended testicles, treatment of varicoceles, prostate surgery, and other testicular or abdominal procedures; mental and psychological factors, including stress levels; exposure to environmental hazards, such as industrial chemicals (benzene, toluene, xylene, pesticides, herbicides, organic solvents, painting materials, and the like), heavy metals, or radiation; the number of fertilized eggs produced using subject's sperm; the number of eggs to which the subject's sperm was exposed; the method of introducing the sperm to eggs (e.g., intrauterine delivery, preparation of the sperm sample, in vitro fertilization (IVF), intracytoplasmic sperm injection (ICSI), etc.); the number of fertilized eggs implanted, the number of fetuses observed at various gestational time points; the number of live births; the health status of the fetus or the newborn; and the like.

The outcome of the test subject may include a likelihood of success in meeting any benchmark included in the outcome data for the training subjects. Thus, for example and without limitation, the outcome of the test subject may include information related to one or more of the following: medications; consumption of alcohol, tobacco, and recreational drugs; diet and dietary supplements, including vitamins; physical activity levels, including exercise and fitness regimens and periods of sitting; frequency of ejaculation; frequency and timing of intercourse, including the temporal relationship between intercourse and other factors; clothing and undergarments; use of hot tubs, baths, saunas, and other environments that expose the testicles to non-physiological temperatures; surgeries, including vasectomies and vasectomy reversals, hernia repairs, correction of undescended testicles, treatment of varicoceles, prostate surgery, and other testicular or abdominal procedures; mental and psychological factors, including stress levels; exposure to environmental hazards, such as industrial chemicals (benzene, toluene, xylene, pesticides, herbicides, organic solvents, painting materials, and the like), heavy metals, or radiation; fertilization procedures, such as preparation or concentration of sperm, artificial insemination, intracervical insemination, intrauterine insemination, intratubal insemination, intrauterine tuboperitoneal insemination, IVF, or ICSI; the likelihood of achieving fertilized eggs, implanted embryos, or embryos or fetuses surviving to any gestational time point, or a live birth; or the likelihood regarding the medical or health status associated with an embryo, fetus, or child. The outcome of the test subject may include a recommended course of treatment, such as a change in one more factors described above or the use of one or more procedures described above.

Figure 7:
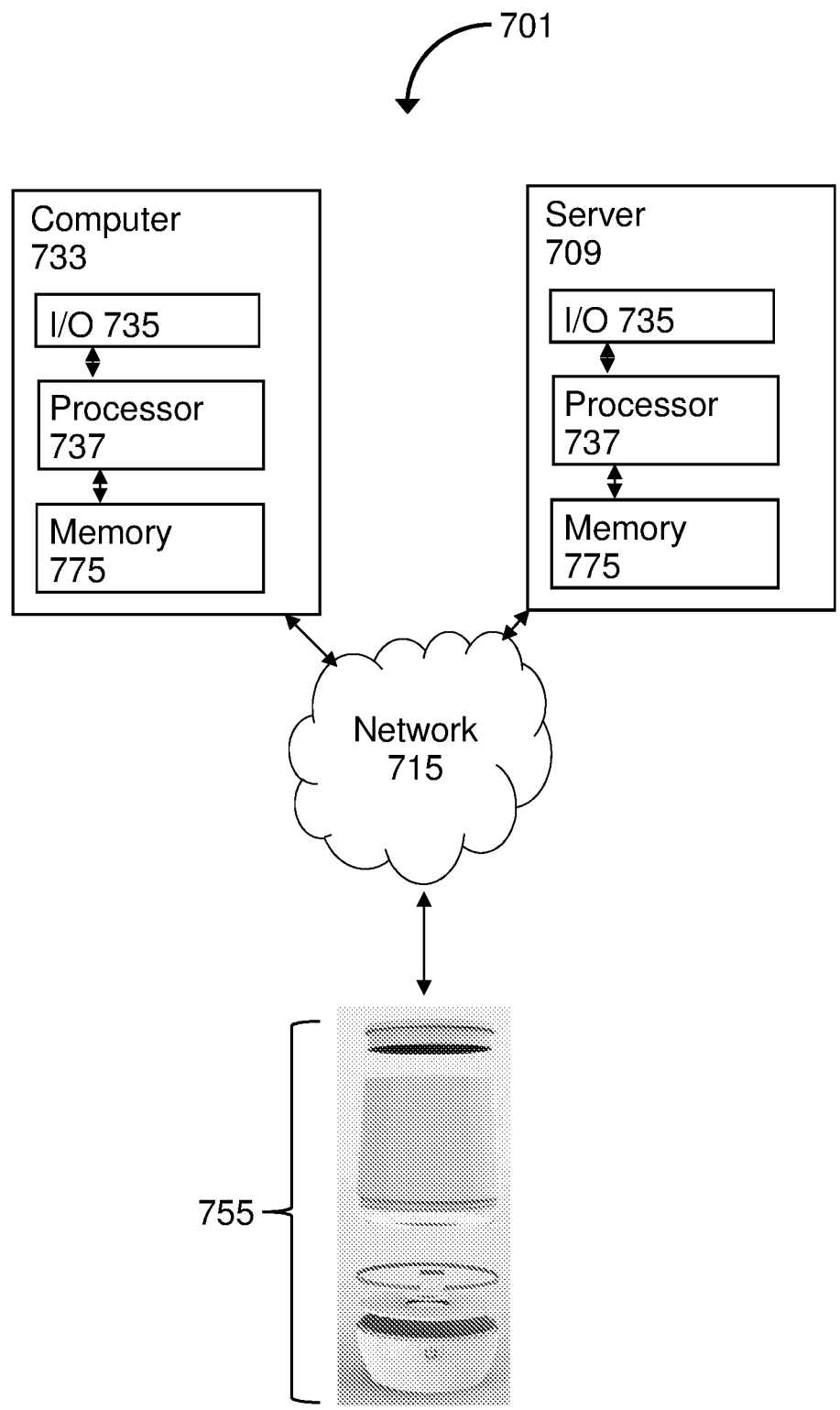
FIG. 7 illustrates a system for performing machine-learning methods of evaluating male fertility according to embodiments of the invention.

FIG. 7 illustrates a system 701 for performing machine-learning methods of evaluating male fertility according to embodiments of the invention. The system 701 includes at least one computer 733. Optionally, the system 701 may include a semen-analysis system 755, such as one described above, e.g., systems 101 and 401, and a server computer 709. Each computer in the system 701 includes a processor 737 coupled to a tangible, non-transitory memory 775 device and at least one input/output device 735. Thus the system 701 includes at least one processor 737 coupled to a memory subsystem 775 (e.g., a memory device or collection of memory devices). The components (e.g., computer, server, and imaging system) may be in communication over a network 715 that may be wired or wireless and wherein the components may be remotely located or located in close proximity to each other. Using those mechanical components, the system 701 is operable to receive or obtain training data, such as semen sample data and outcome data, as well as images of semen sample data generated by the semen analysis system 755 or otherwise obtained. In certain embodiments, the system uses the memory to store the received data as well as the machine learning system data, which may be trained and otherwise operated by the processor.

The memory subsystem 775 may contain one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 701 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Machine learning systems of the invention may be configured to receive images of semen samples and known outcomes, to identify features within the images in an unsupervised manner, and to create a map of outcome probabilities over the features. The machine learning system can further receive images of semen samples from a test subject, identify within the test images predictive features learned from the training steps, and locate the predictive features on the map of outcome probabilities to provide a prognosis or diagnosis.

Any of several suitable types of machine learning may be used for one or more steps of the disclosed methods. Suitable machine learning types may include neural networks, decision tree learning such as random forests, support vector machines (SVMs), association rule learning, inductive logic programming, regression analysis, clustering, Bayesian networks, reinforcement learning, metric learning, and genetic algorithms. One or more of the machine learning approaches (aka type or model) may be used to complete any or all of the method steps described herein. For example, one model, such as a neural network, may be used to complete the training steps of autonomously identifying features and associating those features with certain outcomes. Once those features are learned, they may be applied to test samples by the same or different models or classifiers (e.g., a random forest, SVM, regression) for the correlating steps. In certain embodiments, features may be identified and associated with outcomes using one or more machine learning systems and the associations may then be refined using a different machine learning system. Accordingly some of the training steps may be unsupervised using unlabeled data while subsequent training steps (e.g., association refinement) may use supervised training techniques such as regression analysis using the features autonomously identified by the first machine learning system.

In decision tree learning, a model is built that predicts that value of a target variable based on several input variables. Decision trees can generally be divided into two types. In classification trees, target variables take a finite set of values, or classes, whereas in regression trees, the target variable can take continuous values, such as real numbers. Examples of decision tree learning include classification trees, regression trees, boosted trees, bootstrap aggregated trees, random forests, and rotation forests. In decision trees, decisions are made sequentially at a series of nodes, which correspond to input variables. Random forests include multiple decision trees to improve the accuracy of predictions. See Breiman, L. Random Forests, Machine Learning 45:5-32 (2001), incorporated herein by reference. In random forests, bootstrap aggregating or bagging is used to average predictions by multiple trees that are given different sets of training data. In addition, a random subset of features is selected at each split in the learning process, which reduces spurious correlations that can results from the presence of individual features that are strong predictors for the response variable. Random forests can also be used to determine dissimilarity measurements between unlabeled data by constructing a random forest predictor that distinguishes the observed data from synthetic data. Id.; Shi, T., Horvath, S. (2006), Unsupervised Learning with Random Forest Predictors, Journal of Computational and Graphical Statistics, 15(1):118-138, incorporated herein by reference. Random forests can accordingly by used for unsupervised machine learning methods of the invention.

SVMs are useful for both classification and regression. When used for classification of new data into one of two categories, such as having a disease or not having the disease, a SVM creates a hyperplane in multidimensional space that separates data points into one category or the other. Although the original problem may be expressed in terms that require only finite dimensional space, linear separation of data between categories may not be possible in finite dimensional space. Consequently, multidimensional space is selected to allow construction of hyperplanes that afford clean separation of data points. See Press, W. H. et al., Section 16.5. Support Vector Machines. Numerical Recipes: The Art of Scientific Computing (3rd ed.). New York: Cambridge University (2007), incorporated herein by reference. SVMs can also be used in support vector clustering to perform unsupervised machine learning suitable for some of the methods discussed herein. See Ben-Hur, A., et al., (2001), Support Vector Clustering, Journal of Machine Learning Research, 2:125-137.

Regression analysis is a statistical process for estimating the relationships among variables such as features and outcomes. It includes techniques for modeling and analyzing relationships between a multiple variables. Specifically, regression analysis focuses on changes in a dependent variable in response to changes in single independent variables. Regression analysis can be used to estimate the conditional expectation of the dependent variable given the independent variables. The variation of the dependent variable may be characterized around a regression function and described by a probability distribution. Parameters of the regression model may be estimated using, for example, least squares methods, Bayesian methods, percentage regression, least absolute deviations, nonparametric regression, or distance metric learning.

Association rule learning is a method for discovering interesting relations between variables in large databases. See Agrawal, R. et al., "Mining association rules between sets of items in large databases". Proceedings of the 1993 ACM SIGMOD international conference on Management of data—SIGMOD '93. p. 207 (1993) doi:10.1145/170035.170072, ISBN 0897915925, incorporated herein by reference. Algorithms for performing association rule learning include Apriori, Eclat, FP-growth, and AprioriDP. FIN, PrePost, and PPV, which are described in detail in Agrawal, R. et al., Fast algorithms for mining association rules in large databases, in Bocca, Jorge B.; Jarke, Matthias; and Zaniolo, Carlo; editors, Proceedings of the 20th International Conference on Very Large Data Bases (VLDB), Santiago, Chile, September 1994, pages 487-499 (1994); Zaki, M. J. (2000). "Scalable algorithms for association mining". IEEE Transactions on Knowledge and Data Engineering. 12 (3): 372-390; Han (2000). "Mining Frequent Patterns Without Candidate Generation". Proceedings of the 2000 ACM SIGMOD International Conference on Management of Data. SIGMOD '00: 1-12. doi:10.1145/342009.335372; D. Bhalodiya, K. M. Patel and C. Patel. An Efficient way to Find Frequent Pattern with Dynamic Programming Approach [1]. NIRMA UNIVERSITY INTERNATIONAL CONFERENCE ON ENGINEERING, NUiCONE-2013, 28-30 NOVEMBER, 2013; Z. H. Deng and S. L. Lv. Fast mining frequent itemsets using Nodesets.[2]. Expert Systems with Applications, 41(10): 4505-4512, 2014; Z. H. Deng, Z. Wang and J. Jiang. A New Algorithm for Fast Mining Frequent Itemsets Using N-Lists [3]. SCIENCE CHINA Information Sciences, 55 (9): 2008-2030, 2012; and Z. H. Deng and Z. Wang. A New Fast Vertical Method for Mining Frequent Patterns [4]. International Journal of Computational Intelligence Systems, 3(6): 733-744, 2010; each of which is incorporated herein by reference.

Inductive logic programming relies on logic programming to develop a hypothesis based on positive examples, negative examples, and background knowledge. See Luc De Raedt. A Perspective on Inductive Logic Programming. The Workshop on Current and Future Trends in Logic Programming, Shakertown, to appear in Springer LNCS, 1999. CiteSeerX:10.1.1.56.1790; Muggleton, S.; De Raedt, L. (1994). "Inductive Logic Programming: Theory and methods". The Journal of Logic Programming. 19-20: 629-679. doi:10.1016/0743-1066(94)90035-3; incorporated herein by reference.

Bayesian networks are probabilistic graphical models that represent a set of random variables and their conditional dependencies via directed acyclic graphs (DAGs). The DAGs have nodes that represent random variables that may be observable quantities, latent variables, unknown parameters or hypotheses. Edges represent conditional dependencies; nodes that are not connected represent variables that are conditionally independent of each other. Each node is associated with a probability function that takes, as input, a particular set of values for the node's parent variables, and gives (as output) the probability (or probability distribution, if applicable) of the variable represented by the node. See Charniak, E. Bayesian Networks without Tears, AI Magazine, p. 50, Winter 1991.

The system may include a neural network that facilitates machine learning. The system may include a known neural network architecture, such as GoogLeNet (Szegedy, et al. Going deeper with convolutions, in CVPR 2015, 2015); AlexNet (Krizhevsky, et al. Imagenet classification with deep convolutional neural networks, in Pereira, et al. Eds., Advances in Neural Information Processing Systems 25, pages 1097-3105, Curran Associates, Inc., 2012); VGG16 (Simonyan & Zisserman, Very deep convolutional networks for large-scale image recognition, CoRR, abs/3409.1556, 2014); or FaceNet (Wang et al., Face Search at Scale: 80 Million Gallery, 2015), each of the aforementioned references are incorporated by reference.

Deep learning (also known as deep structured learning, hierarchical learning or deep machine learning) is a class of machine learning operations that use a cascade of many layers of nonlinear processing units for feature extraction and transformation. Each successive layer uses the output from the previous layer as input. The algorithms may be supervised or unsupervised and applications include pattern analysis (unsupervised) and classification (supervised). Certain embodiments are based on unsupervised learning of multiple levels of features or representations of the data. Higher level features are derived from lower level features to form a hierarchical representation. Those features are preferably represented within nodes as feature vectors. Deep learning by the neural network includes learning multiple levels of representations that correspond to different levels of abstraction; the levels form a hierarchy of concepts. In most preferred embodiments, the neural network includes at least 5 and preferably more than 10 hidden layers. The many layers between the input and the output allow the system to operate via multiple processing layers.

Deep learning is part of a broader family of machine learning methods based on learning representations of data. An observation (e.g., an image) can be represented in many ways such as a vector of intensity values per pixel, or in a more abstract way as a set of edges, regions of particular shape, etc. Those features are represented at nodes in the network. Preferably, each feature is structured as a feature vector, an multi-dimensional vector of numerical features that represent some object. The feature provides a numerical representation of objects, since such representations facilitate processing and statistical analysis. Feature vectors are similar to the vectors of explanatory variables used in statistical procedures such as linear regression. Feature vectors are often combined with weights using a dot product in order to construct a linear predictor function that is used to determine a score for making a prediction.

The vector space associated with those vectors may be referred to as the feature space. In order to reduce the dimensionality of the feature space, dimensionality reduction may be employed. Higher-level features can be obtained from already available features and added to the feature vector, in a process referred to as feature construction. Feature construction is the application of a set of constructive operators to a set of existing features resulting in construction of new features.

Within the network, nodes are connected in layers, and signals travel from the input layer to the output layer. In certain embodiments, each node in the input layer corresponds to a respective one of the patches from the training data. The nodes of the hidden layer are calculated as a function of a bias term and a weighted sum of the nodes of the input layer, where a respective weight is assigned to each connection between a node of the input layer and a node in the hidden layer. The bias term and the weights between the input layer and the hidden layer are learned autonomously in the training of the neural network. The network may include thousands or millions of nodes and connections. Typically, the signals and state of artificial neurons are real numbers, typically between 0 and 1. Optionally, there may be a threshold function or limiting function on each connection and on the unit itself, such that the signal must surpass the limit before propagating. Back propagation is the use of forward stimulation to modify connection weights, and is sometimes done to train the network using known correct outputs. For discussion see WO 2016/182551, U.S. Pub. 2016/0174902, U.S. Pat. No. 8,639,043, and U.S. Pub. 2017/0053398, the contents of each of which are incorporated by reference.

The associations between features and outcome (e.g., fertility status) may be represented as a map of outcome probabilities where each identified feature is associated with a likelihood of the known outcome. The correlating step may comprise locating features detected in the test semen sample data on the predictive map of outcomes. The correlated pathology status may provide a prognosis or diagnosis for the test patient from which the test sample was obtained. In certain embodiments, the map of outcome probabilities relates the likelihood of a given outcome for an individual to one or more data points in a semen sample from the individual. The map is established based on features identified in the training data as associated with various outcomes. Preferably, the map of outcome probabilities is created autonomously by the machine learning system. Alternatively, the map may be created or refined with user input.

The map may be created through an iterative process. For example, the map may be updated or refined as new training data is entered into the machine learning system. Consequently, the map may be dynamic. For example, the machine learning system may create an initial map based on a first training set of semen samples and then refine the map based on one or more additional sets of semen sample data. The additional sets of semen sample data may be new sets of training data or sets of data from test subjects for whom outcomes have become known. Subjects for whom outcomes are known may be used as test subjects by withholding outcome data from the trained machine learning system and allowing it to predict outcomes. The known outcomes can then be entered into the machine learning system to re-train it by comparing predicted outcomes to known outcomes for the test/training subjects and create a revised map of outcome probabilities. For example, the map may be refined to eliminate or minimize the incidence of false positive results or false negative results.

The features detected by the machine learning system may be any quantity, structure, pattern, or other element that can be measured from the training data. Features may be unrecognizable to the human eye. Features may be created autonomously by the machine learning system. Alternatively, features may be created with user input.

Where diagnoses or prognoses are provided, they may be provided in a report. Reports may be written or printed reports or may be electronic documents and may be transmitted, for example, to test subjects or to treating physicians either physically or electronically. Diagnoses may indicate an individual's fertility status. The diagnosis may be expressed as a probability or level confidence. The diagnosis may indicate a medical stage of a condition or disease. The diagnosis may include identification of an element in the semen sample data that is associated with low fertility or is amenable to a particular course of treatment. The diagnosis may include a recommended treatment regimen, such those described above.

The machine learning methods for making diagnoses or prognoses regarding the fertility status of a subject or a course of treatment to treat infertility in a subject may combine semen sample data obtained using devices of the invention with other types of data, such as genetic data. In such methods, the machine learning system is provided semen sample data, outcome data, and other data, such as genetic data, during its training phase. If genetic data is used, the trained machine learning system is then provided semen sample data and genetic data about the subject and provides an outcome for the test subject. Genetic data is particularly useful for analysis of fertility status because many genetic aberrations have been associated with infertility or reduced fertility in males.

Figure 8:
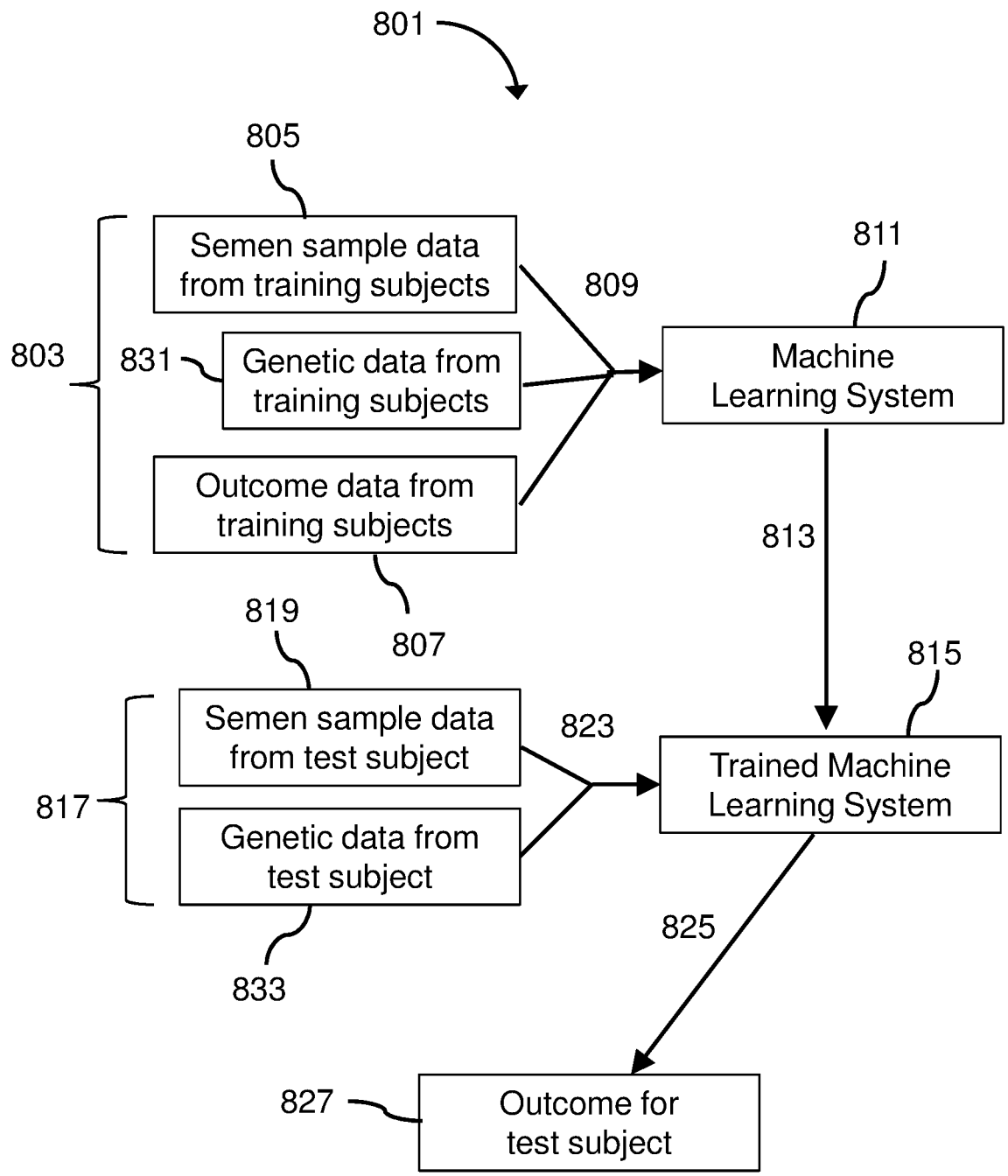
FIG. 8 illustrates a method of evaluating male fertility using a machine learning system to analyze semen sample data and genetic data according to embodiments of the invention.

FIG. 8 illustrates a method 801 of evaluating male fertility using a machine learning system to analyze semen sample data and genetic data according to embodiments of the invention. Training data 803, including semen sample data 805, genetic data 831, and outcome data 807 (e.g., known fertility statuses) from the training subjects is provided 809 to a machine learning system 811. Features are detected within the training semen images by the machine learning system 811, which autonomously learns associations between the features and outcomes, thereby creating 813 a trained machine learning system 815. Test data 817, which includes semen sample data 819 and genetic data 833 from a test subject, is then provided 823 to the trained machine learning system 815. The trained machine learning system 815 detects features in the semen sample data 819 and genetic data 833 from the test subject, correlates them with an outcome (e.g., a fertility status), and provides 825 an outcome 827 for the test subject, such as the likelihood that the test subject will be able to conceive. Any feature described above in relation to machine learning methods of analysis of semen sample data may be applied to machine learning methods of analysis semen sample data in combination with other types of data, such as genetic data.

The genetic data is provided in a format that the machine learning system can process. The methods may include obtaining the genetic data and providing it in a desired format, such as a nucleic acid sequence. The genetic data may be formatted to indicated variations between a nucleic sequence from a subject and a reference nucleic acid sequence, e.g., a sequence taken from a reference human genome, such as hg18 or hg37 as published by the Human Genome Consortium.

The genetic data may relate to male infertility or to a disease or condition associated with male infertility. Mutations in many genes are associated altered male fertility, and the genetic data may relate to one or more of such genes. For example, the genetic data may relate to AMH, AMHR2, AR, ARX, AURKC, BPY, BPY2, CATSPER1, CBX2, CDY, CHD7, DAX1, DAX1, DAZ1, DAZ2, DAZ3, DAZ4, DBY (DDX3Y), DMPK, DMRT1, DNAH11, DNAH5, DNAI1, DPY19L2, ETV5, FANCA, FGFR1, GILZ, GNRH1, HBB, HSF2, HSFY, KAL1, KISS1, KLHL10, LEP, NR5A1 (SF-1), NSMF, PRM1, PRM2, PRM3, PROKR2, PRY, PRY2, RBMY1, RSPO1, SLC26A8, SOHLH1, SOX3, SOX9, SPATA16, SRY, TAC3, TNP2, UBE2B, USP9Y, WT1, or ZPBP. The genetic data may relate to chromosomes or regions or chromosomes associated with altered male fertility, such as the Y chromosome or the azoospermia factor regions, such as AZFa, AZFb, and AZFc, on the Y chromosome. The genetic data may relate to non-coding RNAs, such as miRNAs siRNAs, and piRNAs, that can affect male fertility.

The genetic data provided to the machine learning system in a format that allows the network to identify features associated with cancer. For example, the genetic data may include an array or microarray of SNPs, transcription products, expressed proteins, PCR products or other biomolecules that are fixed onto the solid surface of a readable chip.

The microarray may be read by microscopic analysis of images, for example, as described in Knudsen, Guide to Analysis of DNA Microarray Data, 2004, Wiley and Sons, Print ISBN: 9780471656043. The genetic data may include sequence information provided as a FASTA, FASTQ, Sequence Alignment Map (SAM), Binary Alignment Map (BAM), or VCF file. The genetic data may include variations in gene sequences, exomes, sequenced genomes, transcriptomes, or proteomes in comparison to a reference. For example, a reference sequence may be obtained from Hg38, Hg19, Hg18, Hg17, or Hg16, and the data may indicate variations in relation to one or more of those reference sequences.

The genetic data may include information regarding any type of genetic variation of a gene or gene product, such as a nucleotide or amino acid substitution, insertion, deletion, truncation, translocation, fusion, etc. The genetic data may include one or more single nucleotide polymorphisms (SNPs) from, or portions of sequence from, genes known to be associated with altered male fertility, such as those listed above Other information related to individuals in the training data set or to test subjects may be input into the system. For example, the system may be provided information about therapies administered to the individuals, such as surgeries, procedures, medications, and the like. The information may include duration of therapy, dosage, regimen, or delivery method. The information may include other medically relevant information about the individuals, such as age, weight, height, diet, lifestyle, or family history. Examples of the type of information that may be provided to the machine learning system are provided in Table 1.

TABLE 1

| Information relevant to evaluation of male fertility |
| --- |
| Cancer history/type of cancer/treatment/outcome for subject and family members |
| Age that sexual activity began, current level of sexual activity, including masturbation |
| Smoking history for subject and partner |
| Travel schedule/number of flying hours a year/time difference changes of more than 3 hours (jetlag) |
| Biological age |
| Birth control use |
| Drug use (illegal or legal) |
| Body mass index |
| Alcohol consumption by subject and partner |
| Sleep patterns: number of hours a night, continuous/overall |
| Diet: |
| Exposure to plastics: microwave in plastic, cook with plastic, store food in plastic, plastic water or coffee mugs. |
| Water consumption: |
| Environmental exposure to potential toxins for different regions (extracted from government monitoring databases) |
| Health metrics: autoimmune disease, chronic illness/condition |
| History of sexually transmitted infections: type/treatment/outcome |
| Reproductive hormone levels, e.g., testosterone |
| Stress |
| Age |
| Height and weight |
| Fertility treatment history of subject and partner |
| Twin or sibling from multiple birth (mono-zygotic or di-zygotic) |

The method may include additional steps. For example, the method may include performing an assay to obtain the genetic data from an individual. The assay may include one or more of nucleic acid sequencing, probe hybridization, expression analysis, nucleic acid digestion, nucleic acid mapping, peptide sequencing, and peptide digestion. Techniques for performing these assays are known in the art and can be found, for example, in Molecular Cloning: A Laboratory Manual, Green and Sambrook, eds. Cold Spring Harbor Laboratory Press, 2012.

Figure 9:
FIG. 9 shows an assembled system for analyzing a semen sample according to an embodiment of the invention.

FIG. 9 shows an assembled system 901 for analyzing a semen sample according to an embodiment of the invention. The system includes a receptacle partially contained within a body.

Figure 10:
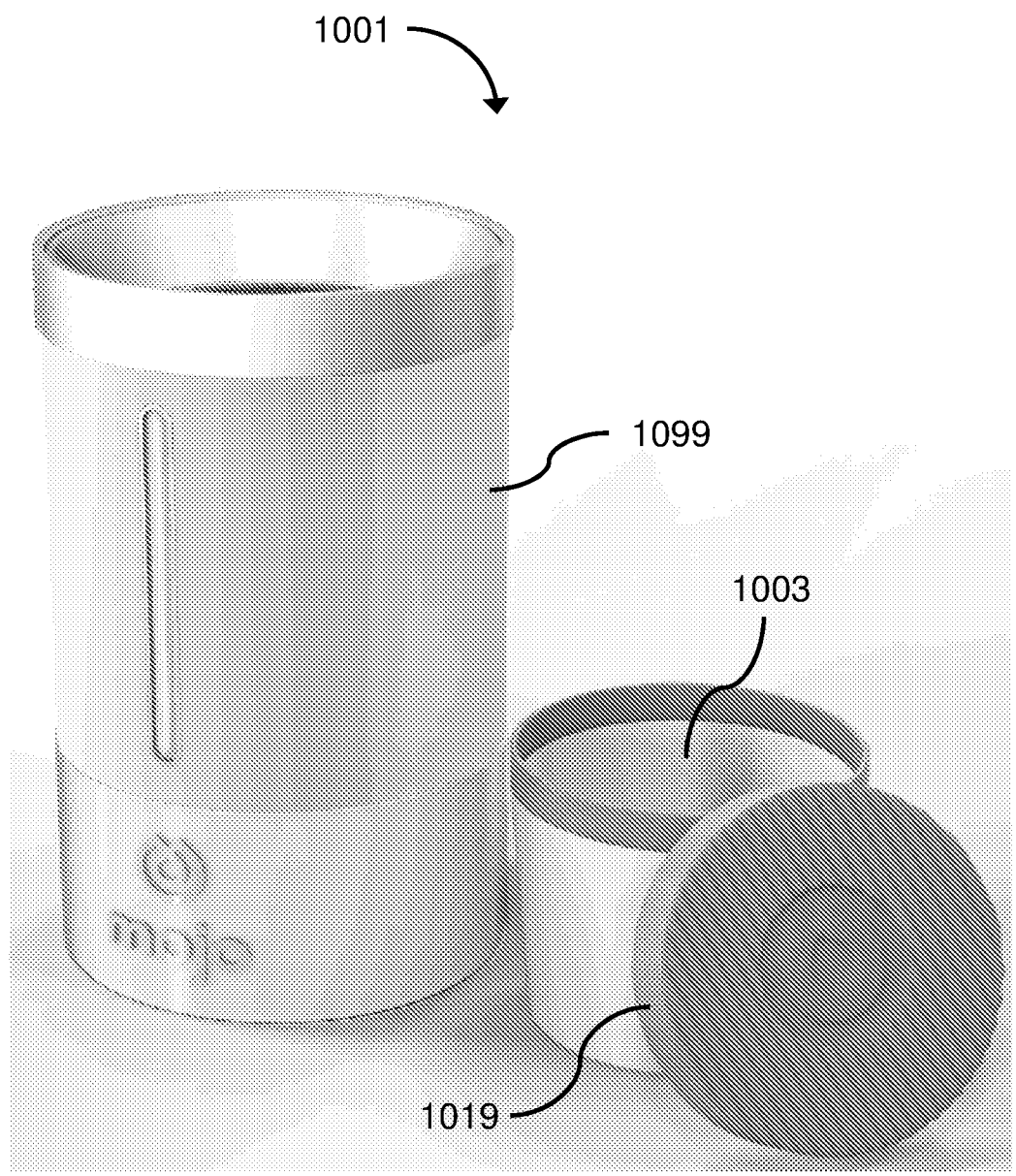
FIG. 10 shows a partially disassembled system for analyzing semen according to an embodiment of the invention.

FIG. 10 shows a partially disassembled system 1001 for analyzing semen according to an embodiment of the invention. The system 1001 includes a receptacle 1003 that is removable from the body 1099 of the system. The receptacle 1003 includes a lid 1019 that can be secured and removed from receptacle 1003, as described above. The receptacle 1003, with or without the lid 1019, may be placed within the body 1099.

Figure 11:
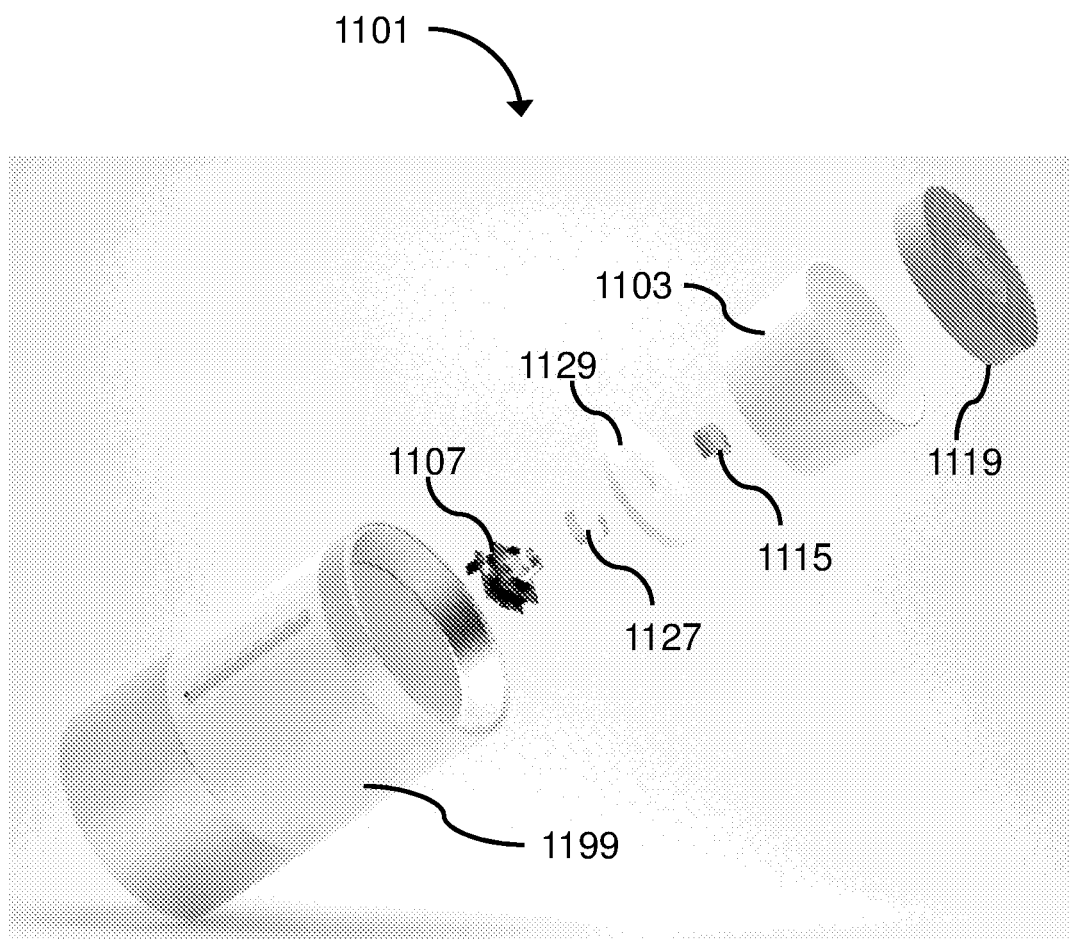
FIG. 11 is an exploded view of a system for analyzing semen according to an embodiment of the invention

FIG. 11 is an exploded view of a system 1101 for analyzing semen according to an embodiment of the invention. They system 1101 includes a lid 1119 that is removable from the receptacle 1103. The receptacle 1103 is removable from the body 1199 and can be partially contained therein. They system also includes a microfluidic element 1115 and an optical device 1107. Separating the microfluidic element 1115 and optical device 1107 is a cover that includes a central, transparent portion 1127 and a peripheral, opaque portion 1129.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A system for analysis of a semen sample, the device comprising:
- a receptacle for collection of the semen sample, the receptacle having an opening that can accommodate at least a tip of a penis;
- a microfluidic element in fluidic communication with the receptacle;
- an analytical device comprising an optical device positioned to interrogate a portion of the semen sample in the microfluidic element; and
- a processor configured to receive optical data from the optical device and determine sperm number, sperm morphology, and sperm motility of the semen sample, wherein determination of sperm morphology comprises an optical analysis of one or more of head size, head shape, midpiece shape, midpiece size, tail shape, tail size, duplicate forms, and cytoplasmic droplets.

2. The system of claim 1, wherein the receptacle is removable from the analytical device.

3. The system of claim 2, wherein the system comprises a pump operably coupled to the receptacle to transport the portion of the semen sample into the microfluidic element.

4. The system of claim 2, wherein the analytical device comprises a lighting system.

5. The system of claim 4, wherein the lighting system comprises:
- a light source; and
- at least one optical fiber configured to transmit light from the light source to the receptacle.

6. The system of claim 4, wherein an interior surface of the receptacle comprises a reflective coating that reflects light from the lighting system to the portion of the semen sample interrogated by the optical device.

7. The system of claim 2, wherein an interior surface of the receptacle comprises a coating that prevents semen from adhering to the interior surface.

8. The system of claim 1, wherein the optical device comprises a CMOS sensor.

9. The system of claim 1, wherein the analytical device comprises a transmitter that is configured to transmit information about sperm number, sperm morphology, or sperm motility of the semen sample to a remote device.

10. A method of analyzing a semen sample from a subject, the method comprising:
providing a device comprising:
- a receptacle for collection of the semen sample, the receptacle having an opening that can accommodate at least a tip of a penis;
- a microfluidic element in fluidic communication with the receptacle;
- an analytical device comprising an optical element positioned to interrogate a portion of the semen sample in the microfluidic element; and
- a processor;

receiving a semen sample into the receptacle directly from the tip of the penis; and automatically determining, via the optical element and processor, sperm number, sperm morphology, and sperm motility information of the semen sample within the device, wherein the method is performed without any external sample preparation steps and the sperm morphology information comprises one or more of head size, head shape, midpiece shape, midpiece size, tail shape, tail size, duplicate forms, and cytoplasmic droplets.

11. The method of claim 10, further comprising transmitting the sperm number, the sperm morphology, and the sperm motility information of the semen sample to a remote device.

12. The method of claim 10, further comprising adding a liquefying agent, surfactant, soap, or detergent to the semen sample within the device.

13. The method of claim 10, wherein the method does not involve heating the semen sample.

14. The method of claim 10, wherein the receptacle is removable from the optical element and the processor.

* * * * *